(12) United States Patent
Oskin et al.

(10) Patent No.: US 6,253,099 B1
(45) Date of Patent: Jun. 26, 2001

(54) CARDIAC MONITORING ELECTRODE APPARATUS AND METHOD

(75) Inventors: Emil Oskin, Natrona Heights; Robert J. Hulings, Mars; Scott D. Quinnell, Kittanning, all of PA (US)

(73) Assignee: Lifecor, Inc., Pittsburgh, PA (US)

( * ) Notice: Subject to any disclaimer, the term of this patent is extended or adjusted under 35 U.S.C. 154(b) by 0 days.

(21) Appl. No.: 09/377,454

(22) Filed: Aug. 19, 1999

(51) Int. Cl.$^7$ .............................. A61B 5/0408; A61N 1/04
(52) U.S. Cl. ...................... 600/372; 600/395; 607/115; 29/825
(58) Field of Search ...................... 600/372, 382–390, 600/395–397; 607/115, 116, 119, 122; 29/825

(56) References Cited

U.S. PATENT DOCUMENTS

| | | | |
|---|---|---|---|
| 2,318,207 | * 5/1943 | Ellis | 600/390 |
| 3,744,482 | * 7/1973 | Kaufman et al. | 600/372 |
| 3,883,846 | 5/1975 | Fletcher et al. . | |
| 4,679,572 | * 7/1987 | Baker, Jr. | 607/127 |
| 4,926,879 | * 5/1990 | Sevrain et al. | 607/152 |
| 5,333,616 | 8/1994 | Mills et al. . | |
| 5,833,714 | * 11/1998 | Loeb | 607/56 |

FOREIGN PATENT DOCUMENTS

| | | | |
|---|---|---|---|
| 2633439 | * 1/1978 | (DE) | 600/396 |
| 396048 | * 11/1990 | (EP) | 600/390 |

OTHER PUBLICATIONS

Kern, Werner, Process for Forming Tantalum Pentoxide Films For Capacitor Applications, Feb., 1996, Pittsburgh, PA.

* cited by examiner

*Primary Examiner*—Lee Cohen
(74) *Attorney, Agent, or Firm*—Buchanan Ingersoll, P.C.

(57) ABSTRACT

An ECG electrode and method of making and using such. The electrode can have a domed electrode element attached to a housing containing an interface disk to which the concave side of the domed electrode connects. Within the housing a signal lead wire has one end attached to the non-skin-contacting side of the dome and another end connected to a signal transition circuit and a buffer amplifier circuit. The domed electrode element can be made by forming a metal disk into a dome and providing an oxide layer over the convex surface of the dome. The convex surface of the domed electrode can ensure reliable ECG signal acquisitions with lower radial forces generally than other electrode types, when positioned adjacent the skin of the patient and when coupled to cardiac activity monitoring equipment and a defibrillator for cardiac sensing capabilities.

49 Claims, 3 Drawing Sheets

PRIOR ART

CARDIAC MONITORING ELECTRODE APPARATUS AND METHOD

BACKGROUND

This invention relates generally to electrodes, for example electrocardiograph (ECG) electrodes, and more particularly, to an electrode having a domed contact surface and a method of making and using such domed electrode.

ECG electrodes are well known in the art and are typically placed in direct contact with a patient's skin in the vicinity of the patient's heart. These electrodes can be used to sense the patient's heart functions.

Conventionally, capacitive electrode elements are flat disks which have been stamped or punched from flat sheets of metal. An example of a once commonly used capacitive ECG electrode is described in U.S. Pat. No. 3,882,846 to Fletcher, et al. Fletcher describes an ECG electrode assembly having an insulated electrode element, which is square-shaped, and an impedance transformer contained in a small plastic housing. Fletcher discloses that the electrode element consists of a thin layer of dielectric material deposited by radio frequency sputtering onto a conductive substrate. Also, the impedance transformer includes an operational amplifier with an FET input stage that is configured to provide a low cut-off frequency. Conductive epoxy is used for the wire connection to the substrate and the electrode is attached to the skin with double-sided adhesive tape. The oxide coating can be, among other types listed, tantalum pentoxide and the substrate materials used include silicon.

In conventional stamping processes, the edges of the electrode element typically have no oxide coating. Unless the bare edges are covered prior to use, an ionic condition can occur with the resultant motion artifacts inherent to a conductive electrode element. Stamping can also create significant burs along the edges of the electrode element which could irritate the skin if not removed. Fletcher accounts for both problems by using an insulating resin to cover the edges of the electrode element. The insulating material covers the burs and may prevent any contact between the skin and the bare substrate of the electrode element.

However, a disadvantage of such flat electrode elements is that they can lose contact intermittently with the skin. Particularly under conditions of patient movement, such as lying down or rolling over while sleeping, the flat electrode element may tilt with respect to the surface of the skin. Consequently, much or all of the active electrode surface may lose contact with the skin. Moreover, the use of an insulating resin, adhesive disk or other means to seal the edges of the electrode element, to prevent the aforementioned ionic condition from occurring, only compounds the intermittent contact problem. The insulating material used to cover the edges also can greatly reduce the active surface area of the electrode, thus increasing the likelihood of loss of contact with the skin if the electrode is tilted.

U.S. Pat. No. 5,333,616 to Mills discloses a flat, dry, skin-contacting electrode made from stainless steel which is plated with 3 micron zones of titanium nitride, titanium carbide or titanium carbonitride. However, this electrode is conductive rather than capacitive and the plating is primarily for wear resistance and appearance.

Accordingly, there is a need for an electrode having a domed electrode element wherein the edge is fully coated or shielded so as to prevent the occurrence of an ionic condition and also which has no burs or such burs are sealed from contact with the skin. Such electrode should, at the same time, provide improved and continuous contact with the skin even if the electrode is substantially tilted with respect to the skin.

SUMMARY

The invention relates to cardiac function sensing electrodes, such as, for example, an ECG electrode having a domed electrode element. The domed electrode element can be attached to a housing which can contain an interface disk to which the domed electrode connects. An annular groove can be formed in the interface disk in which the outer edge of the domed electrode element can be received. A signal lead wire can have one end attached to the non-skin-contacting side of the dome. Another end of the signal lead wire can be connected to a signal transition printed circuit board and a buffer amplifier circuit, which can also be contained within the housing. The transition board provides a termination point for resistors electrically attached to the lead wire in order to provide protection to the buffer amplifier from the high voltage defibrillation pulse. The buffer amplifier stage presents a very high input impedance to the ECG signals produced by the body, and provides a very low output impedance to the system monitor computer and analog module.

Epoxy resin can be used to affix the domed electrode element to the interface disk and the interface disk to the housing. The epoxy resin can also serve to immobilize the signal lead wire by filling the space between the domed electrode element and the signal transition printed circuit board.

To make a domed electrode element according to the invention, a conductive substrate is formed into a dome-shaped element. Next, an oxide layer is formed on the domed surface of the substrate. The oxide layer is preferably formed over the entire domed surface, including the edges and a small portion of the back, non-skin-contacting, side of the dome.

The convex surface of the domed electrode can be positioned against the skin of a patient and the electrode can be coupled to a cardiac activity monitoring device for sensing arrhythmic cardiac conditions. The electrodes can also be coupled to a defibrillator to provide cardiac sensing capabilities.

Separate energy delivery electrodes can also be positioned adjacent the patient's skin for delivery of therapeutic energy from a defibrillator if desired.

Other details, objects and advantages of the invention will become apparent from the following detailed description and the accompanying drawing figures of certain presently preferred embodiments thereof.

BRIEF DESCRIPTION OF THE DRAWING FIGURES

A more complete understanding of the invention can be obtained by considering the following detailed description in conjunction with the accompanying drawings, in which.

DETAILED DESCRIPTION OF CERTAIN EMBODIMENTS

Figure 1:
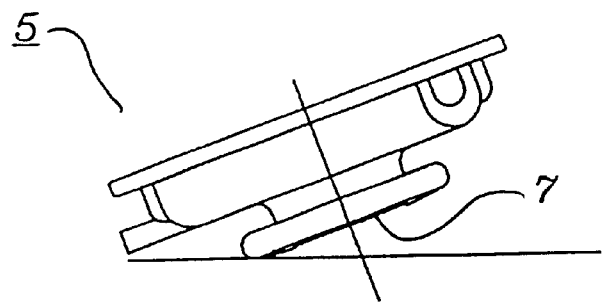
FIG. 1 shows a prior art flat electrode tilted with respect to the skin.

A prior art type capacitive ECG electrode 5 is illustrated in FIG. 1, tilted at an angle to demonstrate how the electrode might be tilted while attached to a patient's skin. Typically, ECG electrodes are generally flat disks 7 which are stamped or punched from flat sheets. This manner of production can result in electrodes with significant burrs at the cut edge.

Also, because the disks are stamped, the electrode element edges typically have no oxide coating. Unless the edges are covered prior to use, with an adhesive disk or by other means, an ionic condition can occur with the resultant motion artifacts inherent to a conductive electrode element.

Figure 2:
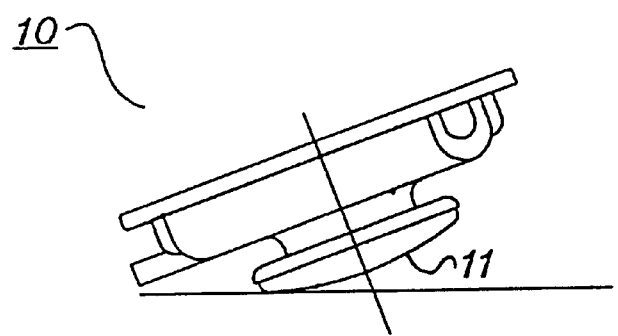
FIG. 2 shows a domed electrode tilted with respect to the skin.

A domed ECG electrode assembly 10 according to the invention is shown in FIG. 2 having a domed electrode element 11 with an oxide layer which is preferably formed over the entire electrode surface, including a skirt portion 30 and an outer edge 12 which results in virtually no ionic characteristics. The outer edge 12 of the domed electrode element 11 can be further sealed against the housing 18 when the two are connected together. Although the domed electrode element 11 is depicted in the drawing figures as having a generally circular base as would be the case where the domed element 11 is formed from a disk, it is to be understood that the base of the domed electrode element 11 can also have other shapes, such as, for example, a square shaped base. In the case of a square base, the dome would be formed from a square sheet of substrate material and could have a pyramid-like shape.

Figure 3:
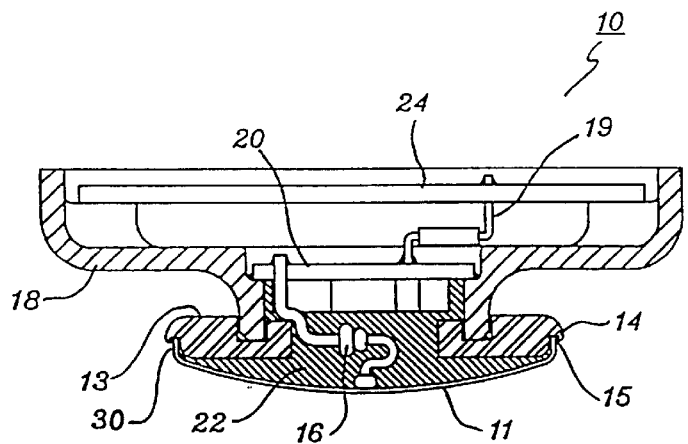
FIG. 3 is a sectional view of the domed electrode shown in FIG. 1.
Figure 4:
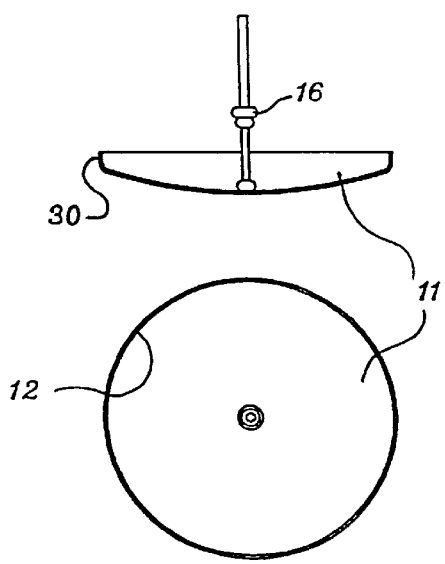
FIG. 4 shows a domed electrode element.
Figure 5:
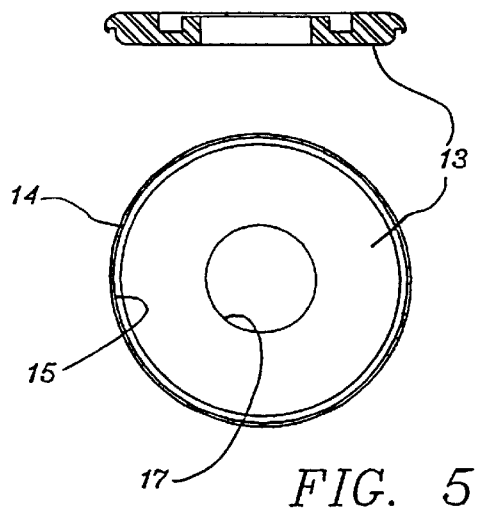
FIG. 5 shows a domed electrode-to-housing interface.

Referring now to FIG. 3, the oxidized domed electrode element 11 can be attached to an electrode interface disk 13. Although the interface 13 is shown having a disk shape, it can have other shapes depending on the shape of the base of the domed electrode element 11 and the housing 18. The signal lead wire 16 can be pre-shaped and welded to the concave inner surface of the domed electrode element 11. The interface disk 13, in turn, can be attached to an electrode housing 18. An opening 17 in the interface disk 13 can be provided through which the signal lead wire 16 can pass and be terminated at a signal transition printed circuit board 20.

The signal transition board provides a termination for the signal lead wire. This wire must be terminated firmly and inhibited from vibration. Due to the high impedance in this part of the circuit, movement of the signal lead wire relative to the remainder of the circuit causes changes in the distributed capacitances in the circuit, thereby introducing unwanted noise onto the desired signal. Another lead wire 19 connects between the signal transition printed circuit board and the ECG buffer printed circuit board 24. The transition board provides a termination point for resistors electrically attached to the signal lead wire in order to provide protection to the buffer amplifier from the high voltage defibrillation pulse. The buffer amplifier stage presents a very high input impedance, approaching 100 megohms, to the ECG signals produced by the body, and provides a very low output impedance to the system monitor computer and analog module located in the defibrillator.

Epoxy resin 22 adhesively attaches the domed electrode element 11 to the interface disk 13. The epoxy 22 also adhesively attaches the interface disk to the electrode housing 18. The buffer amplifier circuit 24 can be attached to the electrode housing 18 with conventional threaded hardware. The domed electrode 11 is inherently a high impedance device, and the buffer amplifier circuit 24 can be utilized primarily as an impedance lowering means. A rear housing cover 26 can be provided over the buffer amplifier circuit 24 and encloses the components contained in the housing 18.

Preferably, the interface disk 13 can have a lip 14 provided around an outer perimeter thereof which forms an annular groove 15. When connected to the interface disk 13, the outer edge 12 of the domed electrode element 11 is received in the annular groove 15. Consequently, any burs which may be present on the outer edge 12 of the domed electrode 11, or any bare spots in the oxide coating, will be enclosed in the annular groove 15 and shielded from contact with the patient's skin.

The domed electrode-to-substrate interconnection is preferably of an all welded construction. Any movement of the signal lead wire 16 relative to the domed electrode 12, prior to the impedance reduction provided by the buffer amplifier 24, produces changes in the distributed capacitance of the buffer amplifier 24 input circuit. This results in significant electrical noise on the desired signal. The design of the electrode housing 18, the attachment of the domed electrode element 11 to the interface disk 13 and the inherent rigidity of the welded connection can virtually eliminate movement of the signal lead wire 16. Additionally, the epoxy resin 22 disposed in the housing 18 further immobilizes the signal lead wire 16 against movement.

Figure 6:
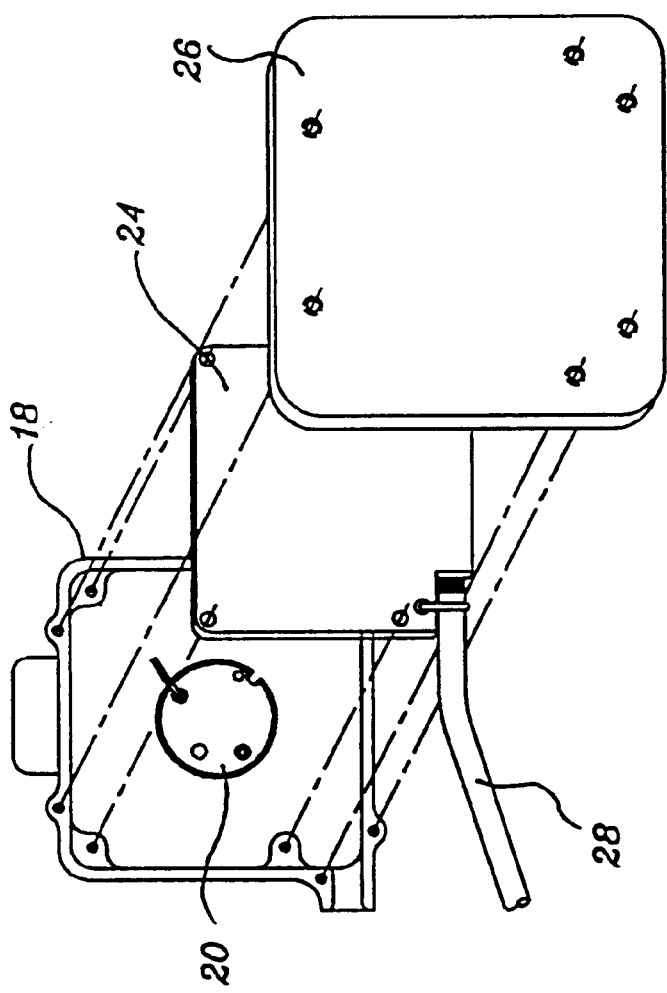
FIG. 6 is an exploded view of a domed electrode housing with a buffer amplifier board and cover.

Referring to FIG. 6, the buffer amplifier printed circuit board 24 can be fastened to the electrode housing 18 in a conventional manner, such as, for example, by threaded hardware. The cover 26 can be similarly fastened to the housing 18. The cover 26 or housing 18 can also have an access opening through which a cable 28 can be connected to the buffer amplifier circuit. The cable 28 can be connected to a device, such as the computer for a cardiac activity monitoring device, for analyzing and displaying information from the domed electrode assembly. A second cable, not shown, can be connected to a defibrillator for delivering a therapeutic pulse to the patient's body, through separate energy delivery electrodes, not shown, which can be of conventional construction.

The domed electrode assembly 10 can preferably be configured to be held in or by a harness for holding the domed electrode against the skin of a patient.

If the domed electrode element 18 should ever need replacement, the electrode housing 18 may be separated from the buffer amplifier printed circuit board 24 and rear cover 26 and discarded. A replacement electrode housing 18, including the attached domed electrode element 11, signal lead wire 16 and signal transition circuit 20 can then be reconnected to the buffer amplifier circuit 24 and rear cover 26. Consequently, the more expensive cabling 28, buffer amplifier circuit 24 and other components of the electrode belt or harness can be retained.

To make the domed electrode 12, a conductive substrate is formed into a dome-like structure having a generally convex skin contacting outer surface and a generally concave inner surface. The dome is preferably formed from a disk-shaped substrate, however, the dome could also be produced from a substrate having other shapes, such as a square or other multi-sided shape. Preferably, the substrate is tantalum metal. An oxide layer can then be formed on the convex surface. Preferably, the oxide layer is a tantalum pentoxide insulating or dielectric layer. An anodizing process can be used to form the oxide layer. The oxide layer preferably covers the entire outer convex surface, the outer edge 12 and a portion of the inner concave surface to ensure that the outer edge 12 is completely sealed. Consequently, the possibility of an ionic condition occurring is virtually eliminated. Moreover, no additional insulating material is necessary to cover or coat the outer edge 12. The epoxy 22, described previously to attach the domed element 1 1, is used only as a structural adhesive and to better immobilize the already robust welded signal lead wire 16 interface.

The human body forms one plate of a capacitor and the domed electrode metal substrate forms the other plate. The method by which prototypical electrodes of this type have been made is an anodizing process using various acids and electrical current flow. Such processes are well known in the prior art. For example, one such process is broadly described in a Technical Report entitled "PROCESS FOR FORMING TANTALUM PENTOXIDE FILMS FOR CAPACITOR APPLICATIONS." This Technical Report was prepared in February 1996, at the Applicants' request, by the consulting firm of WERNER KERN ASSOCIATES, and is hereby incorporated herein by reference.

ECG electrodes are typically held in place against the skin by radial forces provided by an elasticized chest garment or vest. Higher radial forces are typically required for flat electrodes than for the domed electrodes for the same level of signal integrity. Since the electrodes are required to be used by the patient virtually full time, for periods as long as six months, the higher forces can contribute to significant discomfort and may lead to patient non-compliance. The radial forces applied to an electrode housing by a chest garment or vest, and thence to the electrode element, extrudes the skin slightly which ensures adequate electrode-to-skin contact. An electrode having a domed shape aids in this interface contact. The domed shape allows the electrode to better conform to the skin surface under conditions of patient movement during daily activities, or due to changes in chest circumference caused by tissue compression resulting from lying down or rolling over during sleep. The geometry and dimensions of the domed electrode 12 are designed such that the electrode housing 18 may be rotated off the perpendicular to the body by ±20 degrees in any direction and still maintain adequate skin contact for a good signal to noise ratio. Prior art flat electrodes typically cannot be rotated off the skin virtually to any degree and still be expected to maintain adequate skin contact for an acceptable signal to noise ratio unless electrode pressures are excessively high. Any rotation at all will normally cause electrode falloff and the resultant substandard ECG.

Although certain embodiments of the invention have been described in detail, it will be appreciated by those skilled in the art that various modifications to those details could be developed in light of the overall teaching of the disclosure. Accordingly, the particular embodiments disclosed herein are intended to be illustrative only and not limiting to the scope of the invention which should be awarded the full breadth of the following claims and any and all embodiments thereof.

What is claimed is:

1. A electrode element for sensing and treating cardiac conditions, the electrode element comprising:
  a. a conductive substrate formed into the shape of a dome, the dome having a convex surface, a concave surface and an outer edge;
  b. an oxide layer disposed entirely over the convex surface and said outer edge; and
  c. wherein said oxide layer is an insulating material.

2. The electrode element of claim 1 further comprising the oxide layer being additionally disposed over at least a portion of the concave surface of the dome.

3. The electrode element of claim 1 further comprising a signal lead wire attached to the concave surface of the dome.

4. The electrode element of claim 3 further comprising the signal lead wire being welded to the concave surface of the dome.

5. The electrode element of claim 1 wherein the conductive substrate comprises a metal disk.

6. The electrode element of claim 5 wherein the metal disk comprises a tantalum metal disk.

7. The electrode element of claim 1 wherein the oxide layer comprises a tantalum pentoxide insulating layer.

8. The electrode element of claim 1 wherein the oxide layer comprises a tantalum pentoxide dielectric layer.

9. The electrode element of claim 1 further comprising the oxide layer being formed using an anodizing process.

10. The electrode element of claim 1 wherein said insulating material is a dielectric.

11. An electrode assembly for sensing and treating cardiac conditions, the electrode assembly comprising:
  a. a conductive substrate formed into the shape of a dome, the dome having a convex surface, a concave surface and an outer edge;
  b. an oxide layer disposed entirely over the convex surface;
  c. a signal lead wire attached to the concave surface;
  d. a signal transition circuit attached to the signal lead wire;
  e. a buffer amplifier circuit attached to the signal lead wire/signal transition circuit;
  f. a housing containing the signal lead wire, the signal transition circuit and the buffer amplifier circuit;
  g. wherein the dome is connected to a first side of the housing with the concave surface adjacent the housing such that the outer edge is covered by the housing, and the convex surface projecting away from the housing; and
  h. wherein said oxide layer is an insulating material.

12. The electrode assembly of claim 11 further comprising the oxide layer being additionally disposed over the outer edge of the dome.

13. The electrode assembly of claim 12 further comprising the oxide layer being additionally disposed over at least a portion of the concave surface of the dome.

14. The electrode assembly of claim 11 further comprising the lead wire being welded to the concave surface of the dome.

15. The electrode assembly of claim 11 wherein the conductive substrate comprises a metal disk.

16. The electrode assembly of claim 15 wherein the metal disk comprises a tantalum metal disk.

17. The electrode assembly of claim 11 wherein the oxide layer comprises a tantalum pentoxide insulating layer.

18. The electrode assembly of claim 11 wherein the oxide layer comprises a tantalum pentoxide dielectric layer.

19. The electrode assembly of claim 11 further comprising the oxide layer being formed using an anodizing process.

20. The electrode assembly of claim 11 further comprising an interface disk interposed between the concave surface and the housing.

21. The electrode assembly of claim 20 further comprising the interface disk having an annular groove and the outer edge of the dome being disposed in the annular groove.

22. The electrode assembly of claim 11 further comprising a cover connected to a second side of the housing.

23. The electrode assembly of claim 11 further comprising a resin interconnecting at least one of the dome, the interface disk and the signal transition circuit with at least one of each other and the housing.

24. The electrode assembly of claim 23 wherein the resin also immobilizes the signal lead wire within the housing.

25. The electrode assembly of claim 11 further comprising a cable for connecting the electrode assembly to a device for analyzing and displaying patient information.

26. The electrode assembly of claim 11 wherein said insulating material is a dielectric.

27. A method of making an electrode element for sensing and treating cardiac conditions, the method comprising:
   a. forming a conductive substrate into a dome having a convex surface, a concave surface, and an outer edge; and
   b. disposing an insulating material entirely over the convex surface and the outer edge.

28. The method of claim 27 further comprising additionally disposing the insulating material over at least a portion of the concave surface of the dome.

29. The method of claim 27 further comprising attaching a signal lead wire to the concave surface of the dome.

30. The method of claim 29 further comprising welding the signal lead wire to the concave surface of the dome.

31. The method of claim 27 wherein the conductive substrate comprises a metal disk.

32. The method of claim 31 wherein the metal disk comprises a tantalum metal disk.

33. The method of claim 27 wherein the insulating material comprises a tantalum pentoxide insulating layer.

34. The method of claim 27 wherein the insulating material comprises a tantalum pentoxide dielectric layer.

35. The method of claim 27 further comprising forming the insulating material using an anodizing process.

36. The method of claim 27 wherein said insulating material is a dielectric.

37. A method for sensing and treating cardiac conditions in a patient using at least one of cardiac activity monitoring device and a defibrillator, the method comprising:
   a. providing at least one electrode assembly having a domed electrode element;
   b. entirely covering an outer surface and an outer edge of said domed electrode element with an oxide layer, said oxide layer being an insulating material;
   c. positioning said domed electrode element against the skin of a patient such that a convex surface of said domed electrode element is adjacent the skin; and
   d. coupling said electrode assembly to at least one of said monitoring device and said defibrillator to at least one of sense cardiac function and deliver a defibrillation treatment.

38. The method of claim 37 wherein said insulating material is a dielectric.

39. A electrode element for sensing and treating cardiac conditions, the electrode element comprising:
   a. a conductive substrate formed into the shape of a dome, the dome having a convex surface, a concave surface, and a skirt portion having an outer edge;
   b. an oxide layer disposed over the entire convex surface and skirt portion, said oxide layer being an insulating material; and
   c. a housing connectable to said dome at said outer edge, said housing enclosing said outer edge such that all exposed surfaces of said dome are entirely covered by said oxide layer.

40. The electrode element of claim 39 wherein said insulating material is a dielectric.

41. The electrode element of claim 39 further comprising said housing having an annular groove in which said outer edge is received.

42. The electrode element of claim 39 further comprising said oxide layer being additionally disposed over said outer edge.

43. The electrode element of claim 42 further comprising said oxide layer being additionally disposed over at least a portion of said concave surface.

44. The electrode element of claim 39 further comprising a signal lead wire welded to said concave surface.

45. The electrode element of claim 44 further comprising an interface member between said housing and said dome, said interface element having a first side which encloses said outer edge and a second side connectable to said housing.

46. The electrode element of claim 45 further comprising an annular groove in said interface member wherein said outer edge is received.

47. The electrode element of claim 45 a resinous material filling a space enclosed between at least one of said housing, said interface member and said concave surface, said resinous material generally encapsulating said signal wire.

48. The electrode element of claim 47 further comprising said resinous material adhesively joining at least one of said housing, said interface member and said concave surface.

49. The electrode element of claim 47 further comprising said resinous material aiding in immobilization of said signal wire welded to said concave surface.

* * * * *